US00PP28763P2

(12) United States Plant Patent
Giesen

(10) Patent No.: US PP28,763 P2
(45) Date of Patent: Dec. 12, 2017

(54) ***DAHLIA* PLANT NAMED 'DAHZ0002'**

(50) Latin Name: ***Dahlia hybrid* Cav.**
Varietal Denomination: DAHZ0002

(71) Applicant: SYNGENTA PARTICIPATIONS AG, Basel (CH)

(72) Inventor: Eric Giesen, Andijk (NL)

(73) Assignee: Syngenta Participations AG, Basel (CH)

( * ) Notice: Subject to any disclaimer, the term of this patent is extended or adjusted under 35 U.S.C. 154(b) by 130 days.

(21) Appl. No.: 14/757,064

(22) Filed: Nov. 13, 2015

Related U.S. Application Data

(60) Provisional application No. 62/088,968, filed on Dec. 8, 2014.

(51) Int. Cl.
*A01H 5/02* (2006.01)

(52) U.S. Cl.
USPC ..... Plt./321

(58) Field of Classification Search
USPC ..... Plt./263.1, 321
See application file for complete search history.

*Primary Examiner* — Susan McCormick Ewoldt
*Assistant Examiner* — Karen Redden
(74) *Attorney, Agent, or Firm* — Dale Skalla

(57) ABSTRACT

A new *Dahlia* plant named 'DAHZ0002', particularly distinguished by the large, orange double-type flowers, deep green foliage, full and medium sized plant habit with excellent branching, and good floriferiousness.

1 Drawing Sheet

Latin name of the genus and species of the plant claimed: *Dahlia* hybrid Cav.

Varietal denomination: 'DAHZ0002'.

BACKGROUND OF THE NEW PLANT

The present invention comprises a new *Dahlia*, botanically known as *Dahlia* hybrid and hereinafter referred to by the variety name 'DAHZ0002'.

'DAHZ0002' is a product of a planned breeding program. The new cultivar 'DAHZ0002' has large, orange double-type flowers, deep green foliage, full and medium sized plant habit with excellent branching, and good floriferiousness.

'DAHZ0002' originates from a sibling cross hybridization in a controlled breeding program in Andijk, Netherlands. The pollinations were made in August 2007.

The female parent was an unpatented, proprietary hybrid seedling identified as 'D06-100-2', having orange flower color, large flower size, light green foliage color and a large plant habit compared with 'DAHZ0002'.

The male parent of 'DAHZ0002' was an unpatented proprietary plant designated 'D06-204-1', with orange-yellow bi-color flower and smaller plant size than 'DAHZ0002'.

The resulting seeds sown in November 2007 and 'DAHZ0002' was selected as one flowering plant within the progeny of the stated cross in February 2008 in a controlled environment in Andijk, Netherlands.

BRIEF SUMMARY OF INVENTION

Horticultural examination of plants grown from cuttings of the plant initiated in April 2008 in Andijk, Netherlands, and continuing thereafter, has demonstrated that the combination of characteristics as herein disclosed for 'DAHZ0002' are firmly fixed and are retained through successive generations of asexual reproduction.

'DAHZ0002' has not been observed under all possible environmental conditions. The phenotype may vary significantly with variations in environment such as temperature, light intensity and day length.

A Plant Breeder's Right for this cultivar was applied for in the European Community Plant Variety Office (CPVO) on Apr. 22, 2014, No. 2014/1053. 'DAHZ0002' has not been made publicly available more than one year prior to the filing of this application The following traits have been repeatedly observed and are determined to be basic characteristics of the new variety. The combination of these characteristics distinguishes this *Dahlia* as a new and distinct variety.

BRIEF DESCRIPTION OF THE PHOTOGRAPHS

Figure 1:
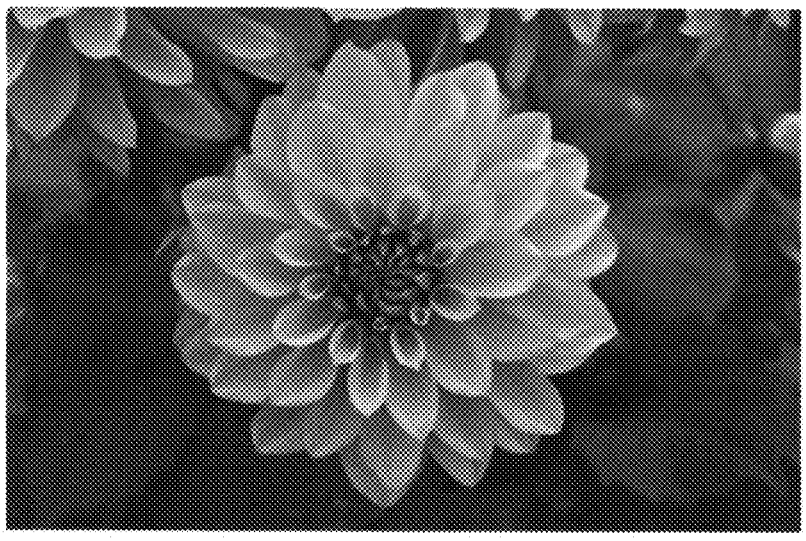
Figure 2:
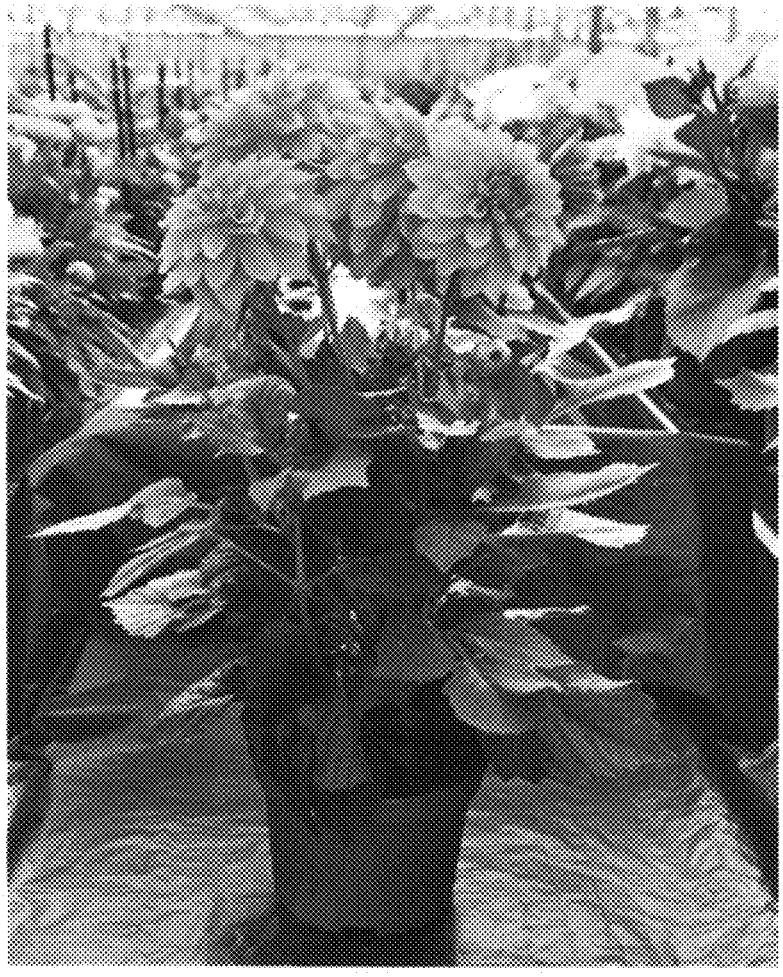

The accompanying photographic drawings show typical flower and foliage characteristics of 'DAHZ0002' with colors being as true as possible with an illustration of this type. The photographic drawings show in FIG. 1, a close-up of the flowers, and in FIG. 2, a flowering potted plant of the new variety.

DETAILED BOTANICAL DESCRIPTION

The plant descriptions and measurements were taken in Enkhuizen, The Netherlands on the $4^{th}$ of September on plants that were growing in the field, outdoors, and were 14 weeks old.

The aforementioned whole plant photograph was taken in April 2012 and the flower close-up was taken at the same time, both Andijk, Netherlands. The plants were growing on benches in a greenhouse trial. They were about 12 weeks of age.

Color references are made to The Royal Horticultural Society Colour Chart (R.H.S.) 2001.

TABLE 1

DIFFERENCES BETWEEN THE NEW VARIETY 'DAHZ0002' AND A SIMILAR VARIETY

| | 'DAHZ0002' | 'Gallery ™ Pablo' U.S. Plant Pat. No. 10,599) |
|---|---|---|
| Overall flower color: | Orange | Light Orange |
| Plant habit: | More vigorous | Less vigorous |
| Number of layers of ray florets: | More, 9 to 10 | Less, 7 to 8 |
| Flower type: | Daisy eyed double | Full double flower |

Plant:

*Form, growth and habit.*—Round, tight and compact; freely branching.

*Plant height.*—28 cm.

*Plant height (inflorescence included).*—35 cm.

*Plant width.*—44 cm.

*Garden performance and tolerance to weather.*—Good.

*Crop time to flowering.*—About 9-12 weeks.

Roots:

*Number of days to initiate and develop roots.*—About 21-28 days at about 21 degrees C.

*Type.*—Fine, fibrous, free branching.

*Color.*—RHS N155B but whiter.

Foliage:

*Arrangement.*—Opposite, simple and sometimes pinnate.

*Immature leaf, color upper surface.*—Between RHS 137B and RHS 137D.

*Immature leaf, color lower surface.*—RHS 137C but more greyish.

*Mature leaf, color upper surface.*—RHS 147A.

*Mature leaf, color lower surface.*—RHS147B but slightly more greyish.

*Type.*—Mostly simple, some are pinnate.

*Length.*—7-10.5 cm, including petiole.

*Width.*—From 4-7.5 cm.

*Shape.*—Ovate.

*Base shape.*—Attenuate.

*Apex shape.*—Acute.

*Margin.*—Dentate.

*Texture, upper surface.*—Glabrous, rough texture.

*Lower surface.*—Glabrous.

*Venation color, upper.*—RHS 147B to A toward the apex.

*Lower.*—RHS 147C.

*Petiole color.*—RHS 144C and RHS 137B on the edges.

*Petiole length.*—Up to 2.2 cm.

*Diameter of petiole.*—0.3 cm at the mid-section.

*Texture.*—Glabrous.

Stem:

*Average quantity of main branches per plant.*—About 8; each with 3 finer branches.

*Color of stem.*—RHS 144A.

*Length of stem.*—20-23 cm.

*Diameter.*—0.5 cm at the midsection.

*Length of internodes.*—5-6 cm.

*Texture.*—Glabrous.

*Color of peduncle.*—RHS N144A, overlain with weak purple tones here and there: RHS 183D.

*Length of peduncle.*—6-7 cm.

*Peduncle diameter.*—0.4 cm.

*Texture.*—Glabrous.

Inflorescence:

*Type.*—Inflorescences borne on terminally above foliage; double-type.

*Blooming habit.*—Continuous throughout the growing season.

*Average quantity of inflorescences per plant.*—65, including buds.

*Average quantity of inflorescences per lateral stem.*—5.

*Lastingness of individual blooms on the plant.*—7-12 days.

*Fragrance.*—None.

Bud (just before opening):

*Color.*—RHS 144A at base; upper part RHS N144A mixed tones of RHS 34A.

*Length.*—1.2 cm.

*Width.*—1.5 cm.

*Shape.*—Completely round turning bell-shaped with the unfolding of the rays.

Immature inflorescence:

*Diameter.*—About 4.5-6 cm.

*Color of ray florets, upper surface.*—RHS 21A.

*Lower surface.*—RHS 45A near base of rays; RHS 26A for the upper part of the rays; and RHS 1A for the veins.

Mature inflorescence:

*Type and shape.*—Double-type, occasionally with a small disk visible.

*Diameter.*—8.0-10.0 cm.

*Depth.*—4 cm.

*Total diameter of 'disc'.*—0.5 cm.

*Receptacle height.*—0.2 cm.

*Receptacle diameter.*—1.3-1.4 cm.

Ray florets:

*Average quantity of florets.*—About 100, arranged in several whorls.

*Shape.*—Broad oval, the outmost ones are almost flat, while the inner ones are funnel-shaped, or, near center, even lanceolate and a little twisted.

*Color of florets, upper surface.*—RHS 1A at the base; mainly RHS 22B for the larger rays with the color becoming deeper towards the center of the inflorescence; RHS 42B for the innermost rays.

*Lower surface.*—RHS 3B at the base; a very light RHS 40D at the apex, RHS 42B for the rays near the centre.

*Length.*—3.2-3.5 cm for the outmost rays; 1-1.5 cm for the innermost rays.

*Width.*—1-2 cm, approximately 0.5cm for the innermost rays.

*Apex shape.*—Almost flat, mucronulate.

*Base shape.*—Fused, forming a tube at the base, acute.

*Margin.*—Entire.

*Texture, upper surface.*—Papillose; glabrous.

*Texture, lower surface.*—Papillose; glabrous.

Disc florets:

*Average quantity of florets.*—About 0 to 5.

*Color of florets.*—RHS 14A.

*Length.*—0.6-0.7 cm.

*Width.*—0.3 cm.

*Shape.*—Tube-shaped.

*Apex shape.*—Acute, 5-pointed.

Receptacle:

*Type of phyllaries*.—Arranged in 2-3 whorls, two different types of phyllaries are developed. Those of the lower whorl are thicker and green in color, while the upper ones are thinner and semi-transparent.

*Phyllaries of the lower whorl*.—

*Average quantity*.—About 5.

*Color, upper surface*.—RHS 137A.

*Color, lower surface*.—RHS 137A.

*Length*.—1.1 cm.

*Width*.—0.7 cm.

*Shape*.—Ovate.

*Base shape*.—Shortly attenuate.

*Apex shape*.—Acute.

*Margins*.—Entire.

*Texture, upper surface*.—Glabrous.

*Lower surface*.—Glabrous.

*Phyllaries in the upper whorl*.—

*Average quantity*.—20-25.

*Color, upper surface*.—RHS 143A at the base to RHS 144C for the upper part, which appears semi-transparent.

*Lower surface*.—RHS 143A at the base to RHS 144C for the upper part, which appears semi-transparent.

*Length*.—1.8 cm.

*Width*.—0.9 cm.

*Shape*.—Ligulate.

*Base shape*.—Fused.

*Apex shape*.—Acute.

*Margins*.—Entire.

*Texture, upper surface*.—Glabrous.

*Lower surface*.—Glabrous.

Reproductive organs:

*Gynoecium*.—Present on ray and disc florets (if a few disk florets are developed). Pistil quantity: 1 per floret. Length: 1.2 cm. Style color: RHS 145C. Style length: 0.9 cm. Stigma color: RHS 21A. Stigma shape: Bi-furchate (bi-lobed). Ovary color: RHS 145A.

*Androecium*.—Present on disc florets only. Stamens quantity: 5 united. Color of filaments: RHS150D. Length filaments: 0.2 cm. Anther color: RHS 21A. Anther length: 0.3 cm. Color of pollen: RHS 21A. Pollen amount: Moderate. Fertility/seed set: Not observed on this hybrid.

Disease/pest resistance: Disease resistance or susceptibility has not been observed on this hybrid.

What is claimed is:

1. A new and distinct variety of *Dahlia* plant named 'DAHZ0002', substantially as illustrated and described herein.

* * * * *